United States Patent [19]
Solum et al.

[11] Patent Number: 5,811,250
[45] Date of Patent: Sep. 22, 1998

[54] METHOD OF DIAGNOSING HAEMASTATIC DISORDERS

[75] Inventors: Nils Olay Solum, N-Nesoddtangen; Frank Brosstad, Oslo; Pal Andre Holme, Oslo; Geir Olay Gogstad, Oslo, all of Norway

[73] Assignee: Nycomed Pharma A/S, Oslo, Norway

[21] Appl. No.: 525,508

[22] PCT Filed: Mar. 23, 1994

[86] PCT No.: PCT/GB94/00592

§ 371 Date: Oct. 4, 1995

§ 102(e) Date: Oct. 4, 1995

[87] PCT Pub. No.: WO94/22018

PCT Pub. Date: Sep. 29, 1994

[30] Foreign Application Priority Data

Mar. 24, 1993 [GB] United Kingdom ................. 9306053

[51] Int. Cl.⁶ ................. G01N 33/53; G01N 33/543; G01N 33/86
[52] U.S. Cl. ................. 435/7.21; 435/4; 435/7.1; 435/7.2; 436/518
[58] Field of Search ................. 435/4, 7.1, 7.2, 435/7.21; 436/518

[56] References Cited

U.S. PATENT DOCUMENTS 5,266,462  11/1993  Hemker et al. ................. 435/13
5,627,036   5/1997  Reutelingsperger ................. 435/7.21

OTHER PUBLICATIONS

George et al., *The Journal of Clinical Investigation*, vol. 78, No. 2, Aug. 1986, pp. 340–348.

Sandberg et al., *The Biochemical Journal*, vol. 203, 1982, pp. 303–311.

Sims et al., *The Journal of Biological Chemistry*, vol. 264, No. 29, 15 Oct. 1989, pp. 17049–17057.

Bode et al., *Blood*, vol. 77, No. 4, 15 Feb. 1991, pp. 887–895.

*Primary Examiner*—Ponnathapura Achutamurthy
*Attorney, Agent, or Firm*—Bacon & Thomas

[57] ABSTRACT

The present invention provides a method of diagnosing haemostatic disorders in a human or non-human subject wherein the presence and/or concentration of platelet-derived microvesicles in a sample of body fluid of the subject is assessed.

17 Claims, No Drawings

METHOD OF DIAGNOSING HAEMASTATIC DISORDERS

The present invention is concerned with the detection and/or measurement of microvesicles derived from blood platelets in a liquid sample such as plasma and the use of this measurement in the diagnosis of haemostatic disorders.

Blood platelets are a normal component of blood and are known to participate actively in haemostatic processes. Through their interaction with the subendothelium of damaged blood vessels, for example, platelets may aggregate to form a primary haemostatic plug. This process is also usually accompanied by the production of various factors involved in haemostasis by the platelets.

Activation of blood platelets greatly enhances their catalysation of haemostatic reactions, and in particular activated platelets demonstrate an increased concentration and activity of factor Va. (Factor Va is a component of the so-called prothrombinase complex which produces thrombin from its precursor prothrombin.) In addition it has been found that platelets shed microvesicles (also called microparticles) from their plasma membrane upon activation. This phenomenon was first described by Sandberg et al. (Biochem. J. 203: 303–311 (1982)).

Following further research, it is now believed that the platelet microvesicles are formed by pinching off or budding of the plasma membrane. The microvesicles contain the platelet glycoproteins Ib, IIb and IIIa and the cytoskeletal proteins filamin, talin and myosin. The microvesicles formed have a diameter of from 50 to 800nm.

Both the microvesicles and the platelets are able to catalyse haemostatic reactions and each display both procoagulant and anti-coagulant activities. Whilst it has been postulated that the formation of microvesicles is linked to production of the prothrombinase complex (see Sims et al., J. Biol. Chem. 264: 17049–17057 (1989)) it has not however been demonstrated that any specific activity is confined either to the platelet derived microvesicles or to the platelets themselves.

Platelet activation and microvesicle formation can be induced by a number of different factors, for example thrombin, collagen, ionophores, calpain and complement protein complexes eg. C5b-9. Weak activators of platelets, for example ADP, epinephrine and platelet activating factor cause only low levels of microvesicle formation. Increased concentration of microvesicles has been demonstrated following storage of platelet concentrates (Bode et al., Blood 77: 887–895 (1991); Solberg et al., Thromb. Res. 48: 559–565 (1987)). Additionally, it has also been shown that stirring of samples comprising platelets activated by collagen and/or thrombin will enhance microvesicle formation.

The formation of haemostasis in causing or reflecting the development of vascular disease or disorders is widely recognised and several haemostatic factors have been examined for their suitability as markers of such disease and disorders. Thus prothrombin time tests involving thromboplastin or activated partial thrombin time tests involving activators for intrinsic plasma coagulation may be used to monitor or to detect disease. Also used are tests for fibrinogen, antithrombin III, protein C, protein S, factor VIII, tissue plasminogen activator, fibrin monomers and fibrinogen degradation products.

As an alternative to the measurement of plasma haemostatic factors, attempts have also been made to monitor the degree of cellular activation taking place during haemostasis. The activation of platelets has been investigated in this regard since (as discussed above) platelets are important participants in haemostasis and are also believed to play a major role in the development of arterial thrombosis and in atherosclerotic processes.

Previous studies have endeavoured to monitor platelet activation by measuring the amounts of proteins secreted. Thus, assays for the measurement of platelet factor 4 (PF-4), β-thromboglobulin (β-TG) and thrombospondin have been investigated (see Lane et al. Thromb. Haemostas. (Stuttgart) 52(2) pages 183–187 (1984)). However, none of these proteins were found to be suitable for routine monitoring. Thrombospondin was found to be non-specific for platelets, and studies on β-TG and PF-4 revealed that their half-lives in the blood were too short, causing problems in distinguishing the sample concentration over the background level. Further, β-TG levels were found to be elevated in patients with renal failure and PF-4 levels were influenced by the presence of heparin (which is extensively used to treat patients with thrombotic disorders).

It has now been recognised that the microvesicles formed by platelets are an accurate indication of platelet activation and so reflect the activity of the haemostatic system as a whole. George et al., (J. Clin. Invest. 78: 340–348 (1986)) monitored the change in glycoproteins appearing on the surface of platelets and on platelet-derived microvesicles following cardiopulmonary bypass surgery. It was noted that the number of microvesicles increased and it was postulated that this was due to the shear stresses that are experienced during such an operation. However it was not suggested that monitoring the concentration of microvesicles would be a good indicator of haemostatic disorders and could provide the basis for a method of diagnosing such conditions It has now been found that assessment of the presence or concentration of platelet-derived microvesicles can be used as a method of diagnosing haemostatic disorders.

The term "haemostatic disorders" includes any abberation or abnormality in the blood clotting cascade mechanism, in particular disorders which lead to increased likelihood of thrombus formation or to a decreased ability for blood clotting following injury for example congenital bleeding disorders, all forms of DIC (Disseminated Intravascular Coagulation) and atherosclerotic disease. Diagnosis of haemostatic disorders thus enables thromboembolic and/or cardiovascular diseases to be detected and/or monitored. This term also includes haemostatic disorders which are a secondary phenomenon, such as for example as a result of cancer.

The present invention thus provides a method of diagnosing haemostatic disorders in a human or non-human subject wherein the presence and/or concentration of platelet-derived microvesicles in a sample of body fluid of said subject is assessed.

The diagnostic method of the invention will be performed in vitro, using a sample of body fluid, eg. blood, obtained from the patient by conventional means.

There is also a need for a simple assay to assess the presence or concentration of platelet-derived microvesicles. It has been found to be particularly advantageous to entrap the microvesicles on a filter allowing easy and convenient measurement.

The present invention thus also provides an assay for the qualitative and/or quantitative determination of platelet microvesicles in a liquid sample, said assay comprising:
  a) i. first filtering the sample, the microvesicles being retained as the retentate and then applying a marker specific to said microvesicles to said retentate; or
     ii. optionally first adding a marker specific to said microvesicles and t hen filtering said sample, the labelled microvesicles being retained as the retentate;

b) optionally washing said filter; and c) determining the presence or amount of marker retained.

The liquid sample should be free from platelets and preferably from other cells able to produce haemostatic proteins eg. epithelial cells or monocytes. It is envisaged therefore that prior to step (a) the liquid sample will be filtered or centrifuged to produce an essentially cell-less sample. A filter having a pore size of greater than or equal to 100nm, for example greater than or equal to 1$\mu$m, is suitable for removing the majority of cells within a liquid sample whilst permitting the much smaller microvesicles to remain suspended. Where the cells within a sample are to be removed by centrifugation, a g-force of 2,000-20,000xg for 10–30 minutes, for example 11,000xg for 15 minutes, is suitable and can be used to produce an essentially cell-free sample as required for step (a) of the assay procedure outlined above. Other equivalent techniques may be used to remove cells and obtain an essentially cell-free liquid sample as required.

In step (a), the filter used should have a pore size small enough to retain the platelet microvesicles and a pore size of less than or equal to 800nm, preferably less than or equal to 200nm, is suitable. By the act of filtration the microvesicles are immobilized upon the filter which may then be contacted with a marker or assessed directly where the microvesicles have already been labelled.

A suitable marker includes any antibody specific to the surface epitopes carried by platelet-derived microvesicles. A preferred antibody marker according to the invention will recognise glycoproteins, including the complex GPIIb-IIIa and/or the separate proteins GPIIb and GPIIIa. Other platelet specific glycoproteins found on microvesicles include GPIb-GPIX, GPIa-IIa and GPIIIb. The antibody binding to the microvesicle may itself be labelled, or alternatively use may be made of a second antibody eg. an anti-mouse immunoglobulin which is labelled and which binds specifically to the first antibody applied eg. a mouse monoclonal antibody. Monoclonal antibodies are preferred. Addition of the marker to the liquid sample as in step (a)(ii) is preferred. The marker may be contacted with the filter immobilized microvesicles according to step (a)(i) either by direct application of the marker to the filter or by immersion of the filter into a solution of the marker. The label used may be any component capable of producing a signal, for example enzymes, chromophores, fluorophores, radioactive isotopes, coloured particles, dyes, colloidal metals etc.

Preferably excess marker is removed by washing the filter before any measurement of the presence or amount of marker is made. Additionally, in step (a)(i), the filter may be washed after application of the sample and prior to addition of the marker. Water or buffer are suitable for the washing steps.

Where the marker used is an enzyme, then step (c) may involve addition of the substrate in the reaction to be catalysed. Preferably however the marker or label used is immediately visible, allowing an immediate assessment to be made.

The concentration of microvesicles within a sample can subsequently be calculated from the level of marker retained on the filter. This value can then be used by the clinician in diagnosing any haemostatic disorder of the patient. An assay permitting quantitative measurement is preferred.

Platelet-free plasma treated with an anticoagulant such as citrate, EDTA or heparin is suitable for use as the sample in the assay according to the invention. The citrated plasma may of course be diluted if required before use.

Additionally the microvesicle containing filter may be analysed for protein content or, more preferably, phospholipid content.

In a preferred embodiment of the invention a nitrocellulose membrane or a nylon membrane, for example HYBOND N® (sold by Amersham International) or MAGNA NYLON® (sold by MSI), respectively, is used as the filter. A pore size of 100nm is convenient. An absorbent pad such as cellulose blotting paper is advantageously placed on one side of the membrane to enhance passage of the liquid sample through the film and a liquid impermeable sheet or frame placed over the other side of the membrane. Circular holes eg. of 5mm diameter, are provided in the impermeable sheet or frame to allow accurate application of the liquid sample and assay liquids to the membrane. A known volume of the cell-free aqueous solution containing the microvesicles (which has optionally been pre-diluted with buffer) eg. 10–500$\mu$l is applied to the membrane and allowed to pass into the absorbent pad underneath. An aqueous solution eg. 10–50$\mu$l of anti-GPIIb-IIIa antibody conjugated to gold-sol colloid as marker is applied and allowed to pass through the membrane. The membrane is then washed with 2×200$\mu$l aliquots of a suitable washing liquid, for example Tris HCl buffer (pH 7.0), before the quantity of gold sol immobilised on the membrane is assessed usually by the naked eye by comparison to a colour scale or by a reflectometer.

The present invention also provides a kit for carrying out the assay of the invention, which comprises at least a filter for retaining the microvesicles from a platelet-free liquid sample and a reagent comprising a marker which selectively labels platelet-derived microvesicles, optionally together with a buffered wash solution.

By subjecting an optionally diluted essentially cell-free plasma sample taken from a human or non-human, preferably mammalian, animal body to the assay described above, the present invention further provides a method of assessing the presence or concentration of platelet-derived microvesicles circulating in the blood.

The following Examples are given by way of illustration only:

All rates given are by volume unless stated otherwise. The following abbreviations are used in the Examples to refer to various buffer solutions:

TS-buffer: 0.01 mol/L Tris-HCl-buffer (pH 7.4)/0.154 mol/L NaCl

TTG-buffer: TS-buffer added 1% Triton X-100

TBS-buffer: 0.02 mol/L Tris-HCl-buffer (pH 7.5)/0.5 mol/L NaCl

TTBS-buffer: TBS-buffer added 0.05% Tween 20.

EXAMPLE 1

Preparation and collection of platelet microvesicles

Blood was collected in buffered aqueous sodium citrate (1:9) and centrifuged at 320xg for 15 minutes. The supernatant containing the platelet-rich plasma (PRP) was transferred to plastic tubes and centrifuged for another 10 minutes at 11,000xg. The resulting supernatant is free of platelets and contains the microvesicles. To collect the microvesicles, 2.8ml of the supernatant was filtered through a MILLEX-VV® 0.10$\mu$m filter (Millipore Products Division, Bedford, Mass., USA) attached to a syringe. The filter was washed extensively in TS-buffer. The microvesicles remaining on the filter could either be further analyzed by processing the entire filter through reaction steps, or they were solubilized in 150$\mu$l TTG-buffer.

EXAMPLE 2

Samples of material from microvesicles solubilised in TTG-buffer were measured with a "Phospholipid enzymatique"

kit (BioMerieux, France) for quantitation of phospholipids. The method is based on Takayama et al., Clin. Chim. Acta., 1977, 79, p.93–98.

EXAMPLE 3

Determination of total protein

Samples of material from microvesicles filtered as described in Example 1 and solubilized in TTG-buffer were measured by the BioRad Dye-binding assay (BioRad, Richmond, USA) based on the method of Bradford, Anal. Biochem. 1976, 72,248-54.

EXAMPLE 4

Rapid test for immunochemical determination of microvesicles

Citrated blood samples were centrifuged at 320xg for 15 minutes followed by centrifugation of the supernatants at 11,000xg for 10 minutes. To the supernatants containing the platelet microvesicles were added monoclonal antibody SC22 directed against an epitope in Cd41b (GPIIb) of the GPIIb-IIIa-complex of platelet surface membranes. The antibody was obtained from Immunotech S.A., Luminy, Marseille, France. The antibody was added at a dilution of 1:1500. After incubation for one minute at 20° C., 2.8 ml of the mixtures were filtered as described in Example 1. The microvesicles with the mouse monoclonal antibody were now trapped on the filters. The filters were extensively washed in TTBS-buffer, and then in TBS-buffer. Goat-anti-mouseIgG F(ab) conjugated to alkaline phosphatase (Jackson Immuno Research Laboratories, USA) diluted 1:3000 in TBS-buffer was flushed through each of the filters. The conjugate was now bound to the antibody attached to the GPIIb-IIIa-complexes in the microvesicles. The filters were immersed in a solution containing 0.5 mg/mL Nitroblue tetrazolium, 0.25 mg/mL 5-bromo-4-chloro-3-indolyl-phosphate-p-toluidine and 0.1 mol/L $NaHCO_3$-buffer (pH 9.8) for a time appropriate to result in measurable colour formation on the filter surfaces.

Patients with positive D-dimer and/or positive soluble fibrin test (ethanol gelation test) were studied using the above-mentioned method. As control was selected an apparently healthy individual with no clinical sign of disease, and with negative D-dimer and soluble fibrin-tests.

The resulting colour on the filters were measured by means of a reflectometer (NYCOCARD® Reader eg. as disclosed in United Kingdom Pat. Nos. 9213733.0 and 9213737.1).

The reflectance values were:

| Sample | Reflectance results | | |
|---|---|---|---|
| | day 1 | day 2 | day 3 |
| Patient | 0.076 | 0.128 | 0.135 |
| Patient | 0.081 | 0.126 | 0.115 |
| Normal | 0.034 | 0.073 | 0.070 |
| Buffer | 0.025 | 0.074 | 0.042 |

It can be seen that the patient samples give substantially higher values than the normal plasma sample and the control buffer.

EXAMPLE 5

Study of material from patients with thromboembolic disease

Patients with thromboembolic disease verified by the presence of D-dimer and/or soluble fibrin in routine laboratory analytical tests, and apparently healthy individuals, were divided in groups depending on age. Blood was collected and centrifuged, and platelet microvesicles were collected on filters as described in Example 1. Analyses of total phospholipid, total protein and GPIIb-IIIa using the rapid immunoassay with specific antibodies (described in Examples 2–4 respectively) were carried out. In the immunochemical assay, the colour obtained with only buffer replacing the sample was used as control and was subtracted from the values. An internal standard of microvesicles were given an arbitrary value of 1.0, and all results obtained with the immunochemical method were related to results obtained with this standard when individual experiments were performed.

The results are presented in Table 1 and show that total protein overlapped considerably between the patients and the healthy individuals. However, the amount of GPIIb-IIIa demonstrated a clear difference between the patients and the healthy individuals. Thus, this analytical method is best suited for construction of a diagnostic tool for detection of platelet microvesicles in blood samples.

The variability in the level of total protein may be due to a variable content of protein within the microvesicles. It may be difficult to control to which extent the vesicles are ruptured through the preparation process, and consequently a variable leakage of soluble proteins from the vesicles may cause the observed variability in the results.

TABLE 1

RESULTS FROM MEASUREMENT OF AMOUNT OF PLATELET MICROVESICLES IN SAMPLES FROM PATIENTS AND NORMAL INDIVIDUALS EMPLOYING TOTAL PHOSPHOLIPID, TOTAL PROTEIN AND AMOUNT OF GPIIb-IIIa

| Age group | | | 20–30 | 30–40 | 40–50 | 50–60 | 60–70 | >70 | Overall | |
|---|---|---|---|---|---|---|---|---|---|---|
| Phospho- | Pas. | X ± SD | 0.27 ± 0.2 | 0.53 ± 0.37 | 0.23 ± 0.16 | 0.53 ± 0.4 | 0.98 ± 0.11 | 0.62 ± 0.54 | 0.50 ± .039 | n = 17 |
| lipid | | range | 0.12–0.50 | 0.25–0.78 | 0.05–0.35 | 0.1–0.9 | 0.9–1.06 | 0.15–1.4 | 0.05–1.4 | |
| (mmol/L) | Healthy | X ± SD | 0.05 ± 0.05 | 0.02 ± 0.02 | 0.02 ± 0.01 | 0.03 ± 0.03 | 0.19 ± 0.16 | — | 0.056 ± 0.09 | n = 30 |
| | | range | 0.008–0.07 | 0–0.09 | 0.008–0.04 | 0.008–0.1 | 0.01–0.4 | — | 0–0.4 | |
| Total | Pas. | X ± SD | 2.3 ± 2.1 | 1.7 ± 1.4 | 1.9 ± 1.2 | 1.2 ± 0.4 | 2.1 ± 0.8 | 0.8 ± 0.3 | 1.59 ± 1.14 | n = 17 |
| protein | | range | 0.7–4.8 | 0.7–2.7 | 1.1–3.3 | 0.7–1.4 | 1.5–2.7 | 0.5–1.2 | 0.5–4.8 | |
| (mg/L) | Healthy | X ± SD | 0.7 ± 0.7 | 0.9 ± 0.6 | 0.6 ± 0.3 | 0.6 ± 0.4 | 0.6 ± 0.3 | — | 0.68 ± 0.48 | n = 32 |
| | | range | 0.1–2.1 | 0.5–2.4 | 0.3–1.0 | 0.3–1.2 | 0.4–1.0 | — | 0.1–2.35 | |
| GPIIB-IIIa | Pas. | X ± SD | 0.44 ± 0.4 | 0.29 ± 0.06 | 0.21 ± 0.2 | 0.45 ± 0.4 | 1.39 ± 0.9 | 0.17 ± 0.15 | 0.46 ± 0.77 | n = 21 |

TABLE 1-continued

RESULTS FROM MEASUREMENT OF AMOUNT OF PLATELET MICROVESICLES IN SAMPLES FROM PATIENTS AND NORMAL INDIVIDUALS EMPLOYING TOTAL PHOSPHOLIPID, TOTAL PROTEIN AND AMOUNT OF GPIIb-IIIa

| Age group | | | 20–30 | 30–40 | 40–50 | 50–60 | 60–70 | >70 | Overall | |
|---|---|---|---|---|---|---|---|---|---|---|
| (arb. units) | | range | 0.12–1.2 | 0.23–0.35 | 0.09–0.45 | 0.12–0.87 | 0.16–3.6 | 0.04–0.52 | 0.09–3.6 | |
| | Healthy | X ± SD | 0.03 ± 0.02 | 0.02 ± 0.02 | 0 | 0 | 0.018 ± 0.004 | — | 0.017 ± 0.04 | n = 32 |
| | | range | 0–0.13 | 0–0.15* | 0 | 0 | 0–0.09* | — | 0–0.15 | |

*Only one value higher than 0.

EXAMPLE 6

Study of material from patients with DIC

Patients with Disseminated Intravascular Coagulation (DIC) as judged from positive tests on fibrin degradation products (FDP) and soluble fibrin (positive ethanol gelation test), were examined using the methods described in the foregoing Examples. The patients were aged between 24 and 72 years. Of the patients with DIC, ten had undergone major surgery, six had preeclampsia, three had sepsis, and three had promyelocytic leukaemia. Controls (n=30) consisted of healthy blood donors matched to age and sex. The DIC patients had receive no anticoagulant therapy when the blood was drawn. Testing for GP IIb-IIIa (eg. GPIIb antigen), phospholipid and total protein with the methods described in the foregoing Examples revealed the following results:

| | | DIC-patients n = 22 | Controls n = 30 | Probability of difference between patients/control |
|---|---|---|---|---|
| GPIIb-IIIa | median | 0.21 ±0.069 | 0.0 | $p < 0.000001$ |
| | range | 0.03–3.59 | 0–0.15 | |
| Phospholipid (mmol/L) | median | 0.43 ±0.167 | 0.015 ±0.006 | $p < 0.000001$ |
| | range | 0.05–1.40 | 0–0.40 | |
| Total protein (mg/ml) | median | 1.45 ±0.61 | 0.6 ±0.028 | $p < 0.001$ |
| | range | 0.5 . 9.98 | 0.10–2.34 | |

The results show that measurement of GPIIb-IIIa and phospholipid distinguish between patients and controls with high significance, whereas the significance is considerably lower with respect to total protein.

We claim:

1. A method of diagnosing haemostatic disorders in a human or non-human subject wherein the presence and/or concentration of platelet-derived microvesicles in a sample of blood or blood products containing microvesicles of said subject is assessed and compared to normal levels wherein higher levels than normal are indicative of haemostatic disorders.

2. A method as claimed in claim 1 including the steps of separating microvesicles from intact cells, immobilizing said microvesicles on a solid support and assessing the presence or concentration of immobilized microvesicles.

3. A method as claimed in claim 2 wherein the microvesicles are separated from intact cells by centrifugation or filtration.

4. A method as claimed in claim 2 wherein the microvesicles are separated from intact cells by filtration through a filter with a pore size ≧200nm.

5. A method as claimed in claim 4 wherein the filter has a pore size ≧1μm.

6. A method as claimed in claim 1 wherein the microvesicles are immobilized on a filter with a pore size ≦200nm.

7. A method as claimed in claim 6 wherein the filter has a pore size ≦200nm.

8. A method as claimed in claim 1 wherein the presence and/or concentration of microvesicles is assessed by binding antibodies to specific microvesicle surface epitopes and assessing the levels of antibodies thus bound.

9. A method as claimed in claim 8 wherein the surface epitopes are carried on glycoproteins.

10. A method as claimed in claim 9 wherein the surface glycoprotein is GPIIb-IIIa.

11. A method as claimed in claim 8 wherein the antibody carries a label which may be detected directly or indirectly.

12. A method as claimed in claim 11 wherein the label is detected indirectly by binding an additional labelled component to the antibody, which may be detected directly or indirectly, or by the addition of substrate to an antibody carrying an enzyme.

13. A method as claimed in claim 1 wherein antibodies to specific microvesicle surface epitopes are bound prior to immobilization.

14. A method as claimed in claim 1 wherein assessment of the presence and/or concentration of microvesicles is made by phospholipid analysis.

15. A method as claimed in claim 2 wherein the solid support is optionally washed between steps.

16. A kit for carrying out the method as claimed in claim 1 comprising at least the following components:

a) a filter for retaining the microvesicles from a platelet-free liquid sample, b) a reagent comprising a marker which selectively labels platelet-derived microvesicles.

17. A kit as claimed in claim 16 wherein the kit additionally contains a buffered wash solution.

* * * * *